United States Patent
Sredni et al.

(10) Patent No.: US 7,629,382 B2
(45) Date of Patent: Dec. 8, 2009

(54) USE OF TELLURIUM CONTAINING COMPOUNDS AS NERVE PROTECTING AGENTS

(75) Inventors: Benjamin Sredni, Kfar-Saba (IL); Michael Albeck, Ramat-Gan (IL)

(73) Assignee: BioMAS Ltd., Kfar-Saba (IL)

( * ) Notice: Subject to any disclaimer, the term of this patent is extended or adjusted under 35 U.S.C. 154(b) by 198 days.

(21) Appl. No.: 11/226,374

(22) Filed: Sep. 15, 2005

(65) Prior Publication Data
US 2006/0063750 A1 Mar. 23, 2006

Related U.S. Application Data

(63) Continuation-in-part of application No. PCT/IB2004/004163, filed on Dec. 15, 2004.

(60) Provisional application No. 60/530,490, filed on Dec. 18, 2003.

(51) Int. Cl.
A61K 31/335 (2006.01)
A61K 31/095 (2006.01)
(52) U.S. Cl. ..................... 514/467; 514/706
(58) Field of Classification Search ................. 514/467
See application file for complete search history.

(56) References Cited

U.S. PATENT DOCUMENTS

| | | | |
|---|---|---|---|
| 3,369,550 A | 2/1968 | Armao | |
| 4,752,614 A | 6/1988 | Albeck et al. | |
| 4,761,490 A | 8/1988 | Albeck et al. | |
| 4,929,739 A | 5/1990 | Sredni et al. | |
| 4,962,207 A | 10/1990 | Albeck et al. | |
| 5,093,135 A | 3/1992 | Albeck et al. | |
| 5,102,908 A | 4/1992 | Albeck et al. | |
| 5,262,149 A * | 11/1993 | Sredni et al. | 424/650 |
| 5,271,925 A | 12/1993 | Sredni et al. | |
| 5,576,347 A | 11/1996 | Sredni et al. | |
| 5,654,328 A | 8/1997 | Sredni et al. | |
| 6,428,534 B1 | 8/2002 | Joye et al. | |
| 6,472,381 B1 | 10/2002 | Albeck et al. | |
| 6,552,089 B1 | 4/2003 | Sredni et al. | |
| 6,747,008 B1 | 6/2004 | Rodgers et al. | |
| 2003/0148970 A1 | 8/2003 | Besterman et al. | |
| 2008/0260770 A1 | 10/2008 | Sredni et al. | |

FOREIGN PATENT DOCUMENTS

| | | |
|---|---|---|
| DE | 4007473 | 9/1991 |
| EP | 0583026 | 2/1994 |
| EP | 583026 | 4/1997 |
| GB | 1427415 | 3/1976 |
| WO | WO 96/18392 | 6/1996 |
| WO | WO 96/18401 | 6/1996 |
| WO | WO 96/06618 * | 7/1996 |
| WO | WO 01/98325 | 12/2001 |
| WO | WO 03/044038 | 5/2003 |
| WO | WO 2005/060341 | 7/2005 |
| WO | WO 2006/030437 | 3/2006 |
| WO | WO 2006/030438 | 3/2006 |
| WO | WO 2006/030439 | 3/2006 |
| WO | WO 2006/030440 | 3/2006 |

OTHER PUBLICATIONS

Delagarza, VW et al. Pharmacologic Treatment of Alzheimer's Disease: An Update. Am Fam Physician 2003; 68: 1365-72.*
Shults CW. Treatments of Parkinson Disease. Arch Neurol. 2003; 60: 1680-1684.*
Boettner, B et al. The role of Rho GTPases in disease development. Gene 286 (2002) 155-174.*
Black et al. "Activation of Interleukin—1β by a Co-Induced Protease", FEBS Letters, 247(2): 386-390, 1989.
Hara et al. "Inhibition of Interleukin 1β Converting Enzyme Family Proteases Reduces Ischemic and Excitotoxic Neuronal Damage", PNAS 94: 2007-2012, 1997.
Hardy "The Secret Life of the Hair Follicle", Trends in Genetics, 8(2): 41-78, 1992.
Examination Report Dated Oct. 29, 2008 From the Government of India, Patent Office Re.: Application No. 2606/CHENP/2006.
Office Action Dated Jan. 26, 2009 From the US Patent and Trademark Office Re.: U.S. Appl. No. 11/663,031.
Dumont "The Interleukin-1 Families of Cytokines and Receptors: Therapeutic Potential for Immunomodulation and the Treatment of Inflammatory Disorders", Expert Opinion in Therapeutic Patents, 16(7): 879-912, 2006.
Iupac "Acyl Groups", Iupac Gold Book, 2 P., Nov. 27, 2007. http://goldbook.iupac.org/A00123.html.
Merck "Human Immunodeficiency Virus (HIV) Infection", Merck Manual Home Edition for Patients and Caregivers, 10 P., May 19, 2008. http://merck.com/mmhe/sec17/ch199/ch199a.html.
Communication Pursuant to Rules 109 and 110 EPC Dated Nov. 20, 2006 From the European Patent Office Re.: Application No. 04801399.9.
International Preliminary Report on Patentability Dated Apr. 26, 2007 From the International Bureau of WIPO Re.: Application No. PCT/IL2005/000991.
International Preliminary Report on Patentability Dated Sep. 28, 2006 From the International Bureau of WIPO Re.: Application No. PCT/IB2004/004163.
International Preliminary Report on Patentability Dated Mar. 29, 2007 From the International Bureau of WIPO Re.: Application No. PCT/IL2005/000989.
International Preliminary Report on Patentability Dated Mar. 29, 2007 From the International Bureau of WIPO Re.: application No. PCT/IL2005/000990.

(Continued)

*Primary Examiner*—Sreeni Padmanabhan
*Assistant Examiner*—Renee Claytor

(57) ABSTRACT

A novel neuroprotective agent is disclosed for the treatment and prevention of neurodegenerative disorders which is based on the administration of an effective amount of a tellurium compound which has a specific ability to induce the differentiation and interfere with apoptotic cell death pathways of neuronal PC-12 cells.

7 Claims, 11 Drawing Sheets

OTHER PUBLICATIONS

International Preliminary Report on Patentability Dated Mar. 29, 2007 From the International Bureau of WIPO Re.: Application No. PCT/Il2005/000992.
Official Action Dated May 14, 2008 From the US Patent and Trademark Office Re.: U.S. Appl. No. 11/663,032.
Official Action Dated Aug. 26, 2008 From the Canadian Intellectual Property Office Re.: Application No. 2,550,459.
Official Action Dated Oct. 27, 2008 From the US Patent and Trademark Office Re.: U.S. Appl. No. 11/663,032.
Official Action Dated May 14, 2008 From the US Patent and Trademark Office Re.: U.S. Appl. No. 11/663,032.
Gross et al. "Tellurium Dioxide Suspension in the Treatment of Seborrhea Capitis", A.M.A. Archives of Dermatology, 78(1): 92-94, 1958.
Jimenez et al. "Interleukin 1 Protects From Cytosine Arabinoside-Induced Alopecia in the Rat Model", esearch Communications, The FASEB Journal, 5: 2456-2458, 1991.
Kalechman et al. "Anti-IL-10 Therapeutic Strategy Using the Immunomodulator AS101 in Protecting Mice From Sepsis-Induced Death: Dependence on Timing of Immunomodulating Intervention", The Journal of Immunology, 169(1): 384-392, 2002.
Kalechman et al. "Inhibition of Interleukin-10 by the Immunomodulator AS101 Reduces Mesangial Cell Proliferation in Experimental Mesangioproliferative Glomerulonephritis", The Journal of Biological Chemistry, 279(23): 24724-24732, 2004.
Makarovsky et al. "Tellurium Compound AS101 Induces PC12 Differentiation and Rescue the Neurons From Apoptotic Death", Annals of the New York Academy of Sciences, 1010: 659-666, 2003.
Shohat et al. "In Vitro Cytokine Profile in Childhood Alopecia Areata and the Immunomodulatory Effects of AS-101", Clinical and Experimental Dematology, 30(4): 432-434, 2005.

Siderowf et al. "Update on Parkinson Disease", Annals of Internal Medicine, 138(8): 651-658, 2003.
Sishi et al. "Defective Production of Interleukin-2 (IL-2) in Patients with Alopecia Areata", Chemical Abstracts, 108: 519, 1988, Abstract.
Sredni et al. "Hair Growth Induction by the Tellurium Immunomodulator AS101: Association With Delayed Terminal Differentiation of follicular Keratinocytes and Ras-Dependent Up-Regulation of KGF Expression", The FASEB Journal, 18(2): 400-402, 2004.
Sredni et al. "The Protective Role of the Immunomodulator AS101 Against Chemotherapy-Induced Alopecia Studies on Human and Animal Models", International Journal of Cancer, 65(1): 97-103, 1996.
International Preliminary Report on Patentability Dated Mar. 29, 2007 From the International Bureau of WIPO Re.: Application No. PCT/IL2005/ 000992.
IPRP (OA 18 Jul. 08).
Official Action Dated Jan. 26, 2009 From the US Patent and Trademark Office Re.: U.S. Appl. No. 11/663,031.
Office Action Dated Jun. 5, 2008 From the Israeli Patent Office Re.: Application No. 176333.
Kalechman et al. "Up-Regulation by Ammonium Trichloro(Dioxoethylene-0,0') Tellurate (AS101) of Fas/Apo-1 Expression on B16 Melanoma Cells: Implications for the Antitumor Effects of AS101", The Journal of Immunology, 161: 3536-3542, 1998.
Sredni et al. "Bone Marrow-Sparing and Prevention of Alopecia by AS101 in Non-Small-Cell Lung Cancer Patients Treated With Carboplatin and Etoside", Journal of Clinical Oncology, 13(9): 2342-2353, 1995.
Wieslander et al. "Antioxidative Properties of Organotellurium Compounds in Cell Systems", Biochemical Pharmacology, 55: 573-584, 1998.

\* cited by examiner

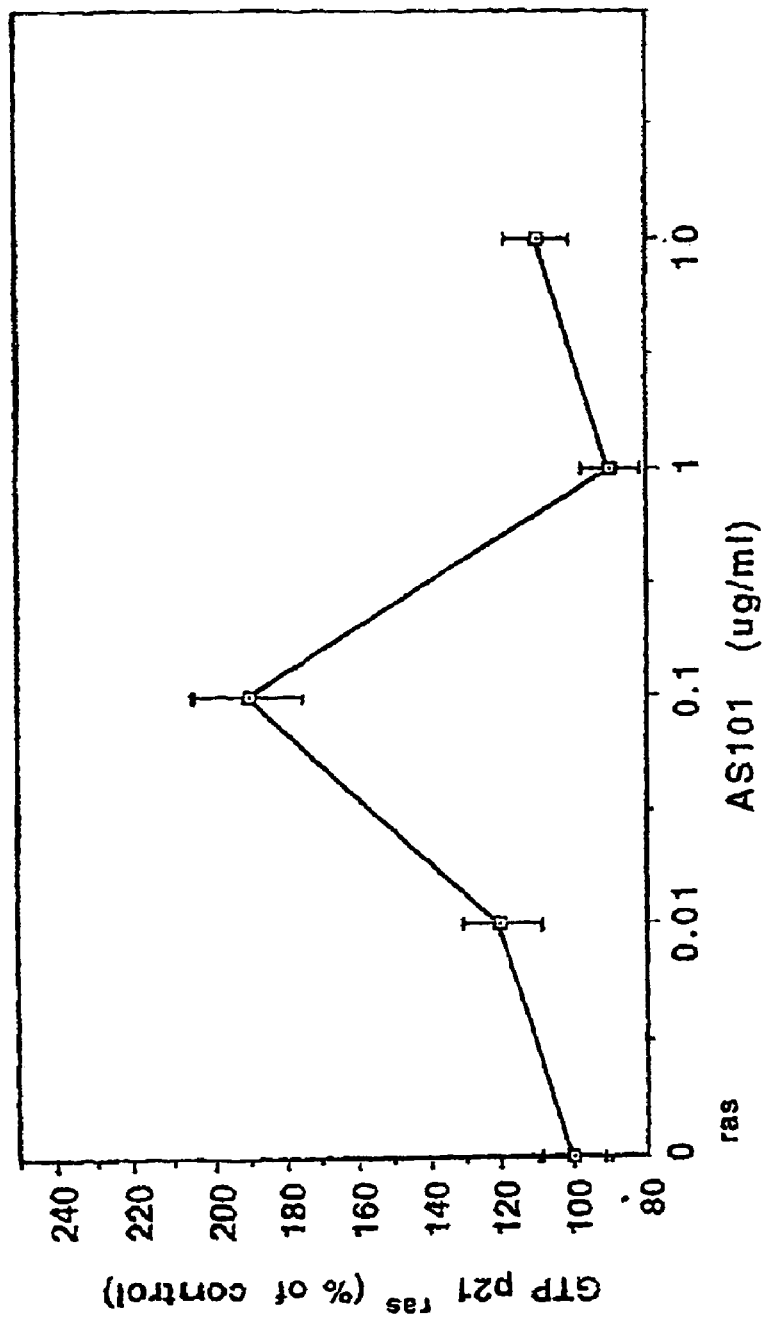
Fig. 1 Activation of p21$^{ras}$ by GDP/GTP Exchange. AS101 Incubated With Recombinant p 21$^{ras}$ for 10 minutes.

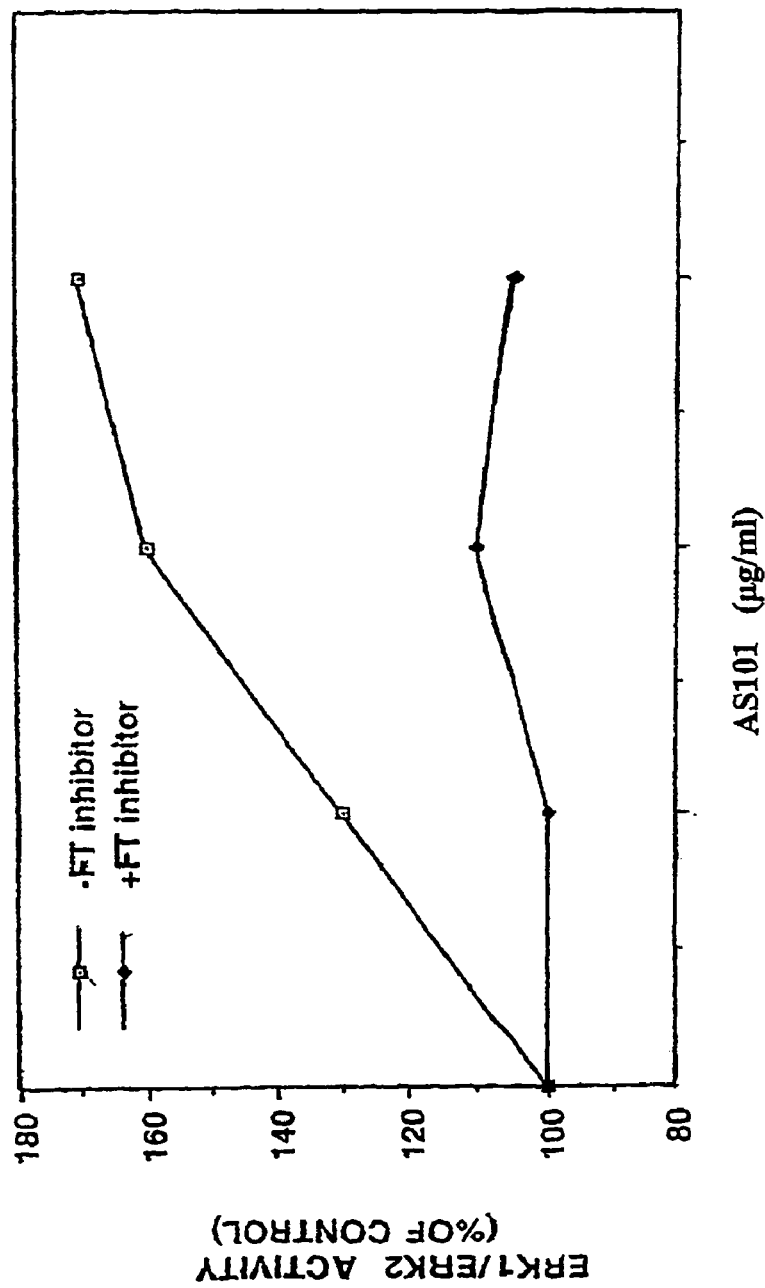
Fig. 2 Activation of ERK1/ERK2 by AS101 Using Myelin Basic Protein as Substrate. N1H3T3 Cells Incubated With AS101 for 10 Minutes With or Without Farnesyl Transferase Inhibitor.

Fig. 3 AS101 Induced Neuritis Outgrowth in PC12 Cells
Fig. 3a PC12WT
CONTROL
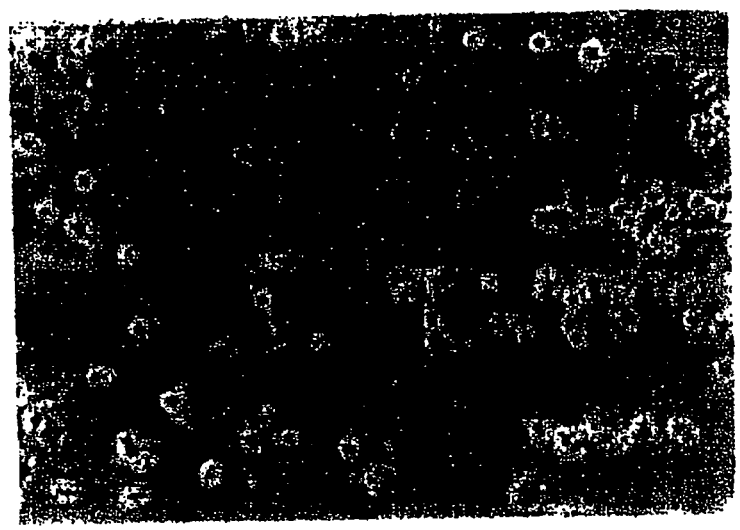
AS101
(0.5 µg/ml)
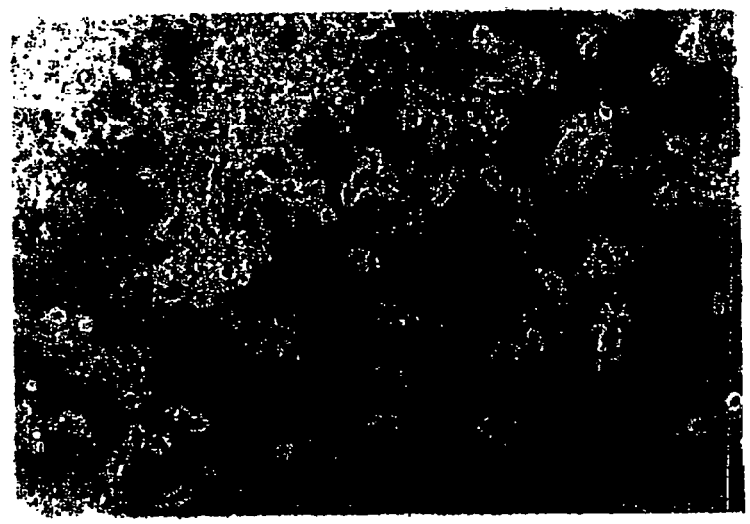
NGF
(100ng/ml)

Fig. 3b N17ras
CONTROL
AS101
(0.5 µg/ml)
NGF
(100ng/ml)

Fig. 3c CYS118
CONTROL
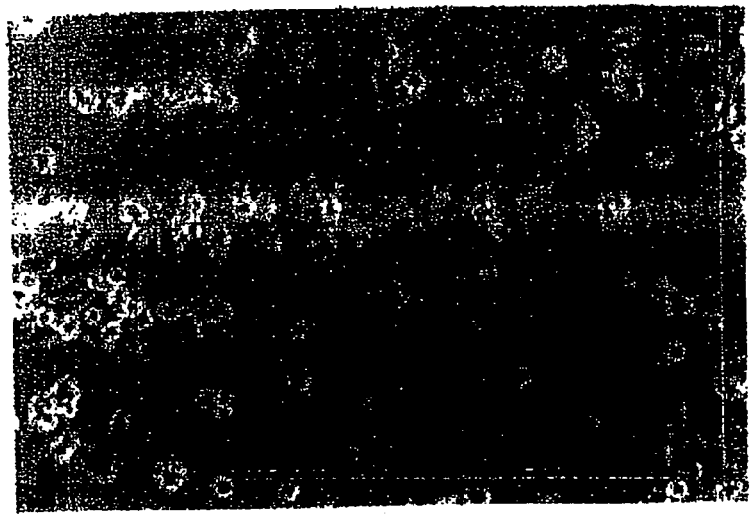
AS101
(0.5 µg/ml)
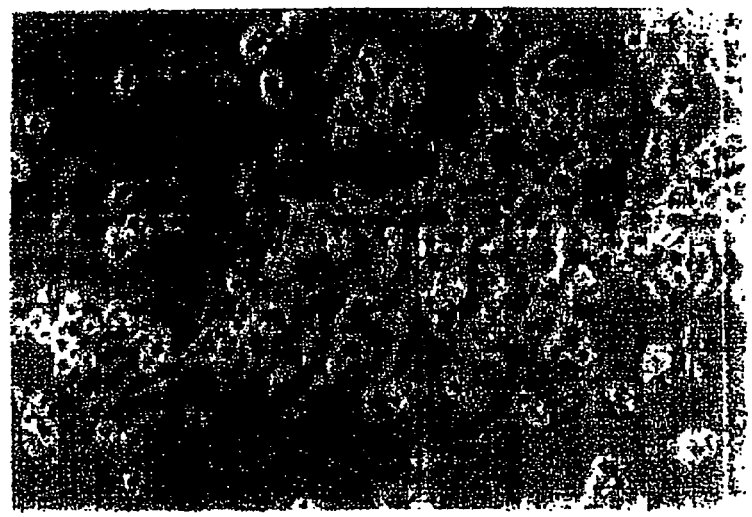
NGF
(100ng/ml)

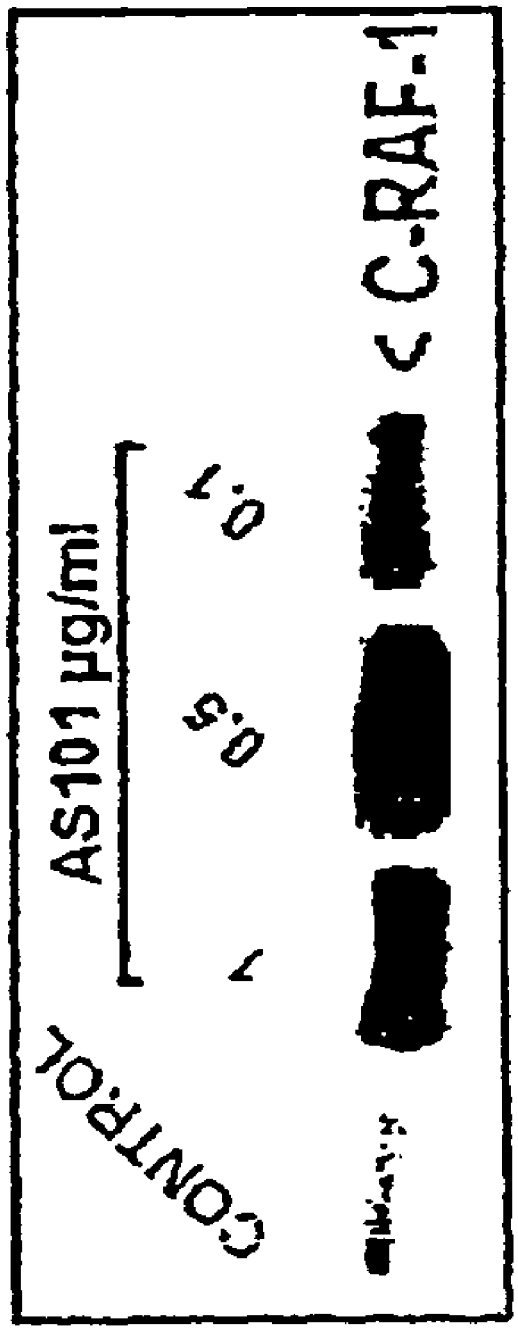
Fig. 4  Cells Incubated With AS101 for 15 minutes

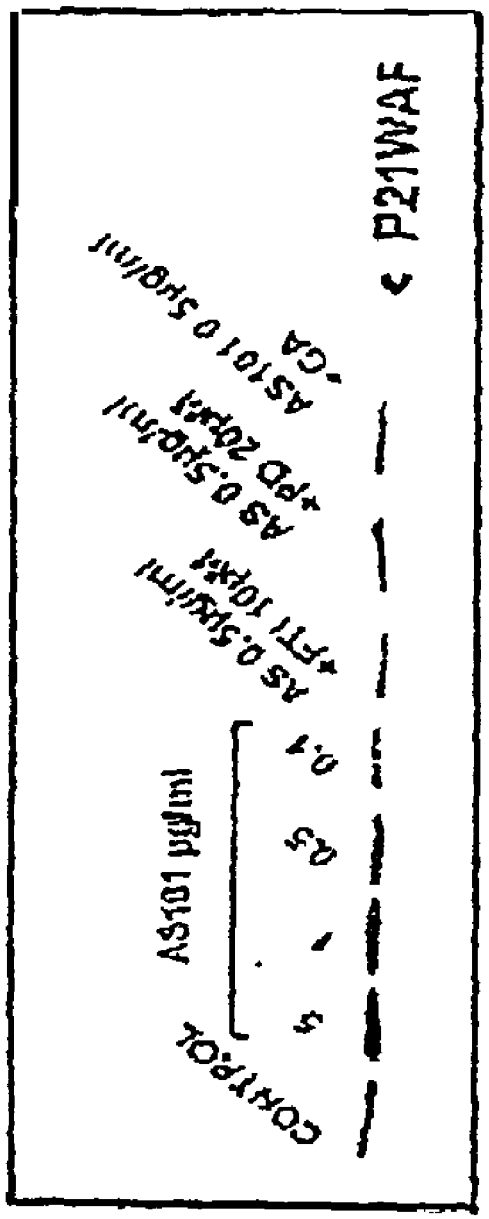
Fig. 5 Cells Incubated With AS101 for 24 hours

USE OF TELLURIUM CONTAINING COMPOUNDS AS NERVE PROTECTING AGENTS

RELATED APPLICATIONS

This application is a Continuation-In-Part (CIP) of PCT Patent Application No. PCT/IB2004/004163, filed on Dec. 15, 2004, which claims priority from U.S. Provisional Patent Application No. 60/530,490, filed on Dec. 18, 2003. The contents of the above Applications are incorporated herein by reference.

FIELD AND BACKGROUND OF THE INVENTION

The present invention relates to novel therapeutic methods and pharmaceutical compositions for treating and preventing neurodegenerative processes and, more particularly, to compositions comprising and methods utilizing tellurium-containing compounds for treating and preventing neurodegenerative processes caused by trauma, such as stroke, accident or surgery, substance abuse, disease, such as neurodegenerative disease and the like.

Neurotrophic factors are proteins which are responsible for the growth and survival of neurons during development, and for maintaining adult neurons. Neurotrophic factors are also capable of promoting regrowth of damaged neurons in vitro and in animal models. The possibility of treating degenerative diseases with neurotrophic factors has motivated research for dopaminotrophic factors. Several neurotrophic factors, such as basic fibroblast growth factor (bFGF), epithelial growth factor (EGF), insulin-like growth factor (IGF), and brain-derived neurotrophic factor (BDNF), have shown promise in the rescue of dopaminergic neurons in vitro. However, their effectiveness in vivo has been for the most part somewhat less promising. Neurotrophic factors often cannot reach their target receptors since they rapidly degrade in the blood stream and cannot pass through cell membranes or the blood brain barrier. Alternatively, glial-derived neurotrophic factor (GDNF) has been found to specifically enhance the survival of midbrain dopaminergic neurons in vitro and exert a protective effect on degenerating dopaminergic neurons in vivo. Similarly, insulin-like growth factor 1 (IGF-1) has been found to prevent brain cells from dying after an asphyxial or ischemic brain insult.

Evidence now shows that some drugs can stabilize, reinforce or even regenerate neurotubules within the central or peripheral neurons of a human nervous system. Certain drugs, such as brimonidine and various beta-adrenergic blocking agents, have been accepted as neuroprotective drugs that can protect the central nervous system from acute ischemia and crush trauma in humans. While certain methods and chemical compositions have been developed which aid in inhibiting, remitting, or controlling neurodegeneration, new neuroprotective methods and pharmacotherapeutic agents which are able to slow or stop such neurological damage are needed. There is a great need for additional compounds useful in treating a variety of neurological conditions.

Neurodegenerative processes are generally characterized by the long-lasting course of neuronal death and the selectivity of the neuronal population or brain structure involved in the lesion. The reasons for such specificity are largely unknown, as are the general mechanisms of the diseases. One common feature of these diseases, however, is that neuronal death is thought to involve apoptosis, at least in part.

Neuronal apoptosis is a programmed cell death mechanism, which is required for normal development of the nervous system, but which also occurs in pathological states. Extensive cell death is observed after acute brain injury, including stroke and trauma, and is thought to contribute to neurodegenerative diseases such as Parkinson's disease and Alzheimer's. Cerebral infarctions such as cerebral thrombosis and embolism are triggered by ischemia of the brain due to stenosis of blood vessels, brain thrombi or brain emboli. Treatment consists of anti-edema agents, such as mannitol, which improve post-ischemic cerebral edema; and thrombolytic agents, such as alteplase or urokinase, which do not effect neuronal death or exert a neuroprotective effect. In Parkinson's disease, there is selective degeneration of dopaminergic neurons in the nigrostriatal pathway. Treatment with L-dopa does not arrest progress of the disorder in dopaminergic neurons. Pharmacotherapeutic agents are needed to prevent apoptosis or death of the dopaminergic neurons in Parkinson's disease. Similarly, in Alzheimer's disease, a neurodegenerative disease characterized by the deposition of amyloid senile plaques, neurofibrillary tangle formation and cerebrum atrophy, apoptosis is involved in the mechanism of neuronal death in dementia in these patients. Pharmacotherapeutic agents are generally held to have little efficacy in Alzheimer's dementia.

The neurotrophin family of soluble peptide factors is required for the correct development and differentiation of the nervous system. Neutrotrophins bind receptor tyrosine kinases and activate a variety of intracellular signaling molecules which are necessary for neuron survival and differentiation.(Ebadi M., Bashir R. M., Heidrick M. L. et al, 30 Neurochem Int. 347 [1997]). The identification of the specific molecules involved in vivo has attracted considerable attention. Due to the relative difficulty of studying signaling in neurons, neurotrophin signaling has been primarily studied using the pheochromocytoma PC12 cells as a model system. This cell line has proved useful for studying mechanisms of neuronal survival, differentiation, and cell death. PC12 cells respond to NGF exposure by differentiating to resemble sympathetic neurons. Upon NGF exposure, PC12 cells cease division, extend neuritis, become electrically excitable and express neuronal markers. Withdrawal of trophic support, either by serum deprivation of proliferating neuroblast-like PC12 cells or by NGF/serum removal from neuronally differentiated cells, leads to their apoptotic death. NGF withdrawal similarly triggers death of sympathetic neurons both in vivo and in vitro.

Two signaling cascades have so far been implicated as being involved in the differentiation and survival of PC12 cells upon binding of neurotrophin: activation of the ras/erk pathway (Nakamura, T., Sanokawa, R., Sasaki, Y., et al., 13 Oncogene 1111 [1996]) and P13 Kinase/Rac signaling (Raffioni, S., Bradshaw, R. A., 89 Proc. Natl. Acad. Sci. 9121 [1992]).

The ras/erk signaling pathway appears to be extremely important in mediating NGF-induced differentiation of PC12 cells. Both ras and its signaling intermediates raf, mek and erk kinases are critical for this activity (Cowley, S., Patterson, H., Kemp, P. et al., 77 Cell 841 [1994]). This has been demonstrated by studies showing NGF independent differentiation of PC12 cells expressing constitutively active forms of these intermediates, or inhibition of NGF-induced differentiation by expression of their dominant interfering forms. The erk pathway has been implicated in NGF-mediated PC12 cell survival (Xia, Z., Dickens, M., Raingeaud, J. et al., 270 Science 1326 [1995]), and seems to be required for NGF mediated cell cycle arrest. Protection of neuronal cells from death evoked by withdrawal of trophic support by agents such as N-acetyl cysteine has been shown to be mediated by the activation of the ras/erk pathway, and not by their antioxidative properties. In response to loss of trophic support, PC12 and other cell types show an increased JUN kinase (JNK) activity. Evidence has been provided with PC12 cells that this increase is required for death, and a model has been proposed in which survival occurs when the elevation of JNK activity is suppressed and erk kinase activity is stimulated (Id.). JNK/p38 activates the ICE proteases, thereby leading to apoptotic cell death. Previous studies have shown that multiple molecules prevent the death of naive and neuronal PC12 cells deprived of trophic support. Bc12 has been shown to protect assorted cell types from death evoked by various stimuli. In particular, this protein suppresses death of PC12 cells and sympathetic neurons induced by withdrawal of trophic support, probably via inhibition of JNK and suppression of cytochrome c release from mitochondria, followed by inhibition of caspases. It therefore follows that interference with one or more of the signaling molecules that participate in the pathways that lead to apoptotic death will confer protection from loss of trophic support or other stress conditions.

One of the causes of neurodegenerative disorder is trauma, such as for example, spinal cord injury. Nerve cells of the central nervous system (CNS) i.e., the brain and spinal cord respond to insults differently from most other cells of the body, including those in the peripheral nervous system. The brain and spinal cord are confined within bony cavities that protect them, but also render them vulnerable to compression damage caused by swelling or forceful injury. Cells of the CNS have a very high rate of metabolism and rely upon blood glucose for energy. The "safety factor," that is the extent to which normal blood flow exceeds the minimum required for healthy functioning, is much smaller in the CNS than in other tissues. For these reasons, CNS cells are particularly vulnerable to reductions in blood flow (ischemia). Other unique features of the CNS are the "blood-brain-barrier" and the "blood-spinal-cord barrier." These barriers, formed by cells lining blood vessels in the CNS, protect nerve cells by restricting entry of potentially harmful substances and cells of the immune system. Trauma may compromise these barriers, perhaps contributing to further damage in the brain and spinal cord. The blood-spinal-cord barrier also prevents entry of some potentially therapeutic drugs. Finally, in the brain and spinal cord, the glia and the extracellular matrix (the material that surrounds cells) differ from those in peripheral nerves. Each of these differences between the PNS and CNS contributes to their different responses to injury.

In addition to the initial injury involved in damage to the spinal cord following g trauma, delayed, secondary damage occurs. One of the main contributing factors involved in such secondary damage is cell death, either by necrosis or apoptosis. Furthermore, it is believed that the immune system also plays a role in the neurodegeneration resulting from CNS trauma *NIH Workshop: Spinal Cord Injury*, September 1996. Most types of immune cells enter the CNS only rarely unless it has been damaged by trauma or disease. Microglial cells, which are normally found in the CNS, have some immune functions and become activated in response to damage. Following trauma, other types of immune cells react to signals from damaged tissue and changes in endothelial cells by entering the CNS. Neutrophils are the first type of immune cells to enter the CNS from the rest of the body. These cells enter the spinal cord within about 12 hours of injury and are present for about a day. About 3 days after the injury, T-cells enter the CNS. The key types of immune cells in spinal cord injury appear to be macrophages and monocytes, which enter the CNS after the T-cells. These cells scavenge cellular debris. One type of macrophage, the perivascular cell, may also mediate damage to the endothelial cells that line blood vessels. It is not clear which signals control the entry of immune cells into the CNS, but changes in cell adhesion molecules most likely play an important role.

The action of immune cells once they enter the damaged spinal cord is poorly understood. Some cells engulf and eliminate debris as they do during inflammation in other parts of the body. Macrophages, monocytes, and microglial cells release a host of powerful regulatory substances that may help or hinder recovery from injury. Potentially beneficial substances released by these cells include the cytokines TGF-beta and GM-CSF (transforming growth factor-beta and granulocyte-macrophage colony-stimulating factor) and several other growth factors. Apparently detrimental products include cytokines such as TNF-alpha and IL-1-beta (tumor necrosis factor-alpha and interleukin-1-beta) and chemicals such as superoxides and nitric oxide that may contribute to oxidative damage. Again, it is unclear what is helpful and harmful about many of these powerful substances in the context of the injured spinal cord.

Use of methylprednisolone, Naloxone or Tirilazad has been reported for treatment of damage caused by spinal cord trauma. Known side-effects of methylprednisolone include allergic reaction, which may result in breathing difficulties, closing of the throat, swelling of the lips, tongue or face, or hives; increased blood pressure, resulting in severe headache or blurred vision, and sudden weight gain. Side-effects of naloxone include allergic reaction, as for methylprednisolone; chest pain or fast irregular heartbeats; seizures, difficulty breathing; and fainting.

Various tellurium compounds, having immunomodulating properties, have been shown to have beneficial effects in diverse preclinical and clinical studies. A particularly effective family of tellurium-containing compounds is taught, for example, in U.S. Pat. Nos. 4,752,614; 4,761,490; 4,764,461 and 4,929,739, whereby another effective family is taught, for example, in a recently filed U.S. Provisional Patent Application No. 60/610,660, which are all incorporated by reference as if fully set forth herein. The immunomodulating properties of this family of tellurium-containing compounds is described, for example, in U.S. Pat. Nos. 4,962,207, 5,093,135, 5,102,908 and 5,213,899, which are all incorporated by reference as if fully set forth herein.

One of the most promising compounds described in these patents is ammonium trichloro(dioxyethylene-O,O')tellurate, which is also referred to herein and in the art as AS101. AS101, as a representative example of the family of tellurium-containing compound discussed hereinabove, exhibits antiviral (*Nat. Immun. Cell Growth Regul.* 7(3):163-8, 1988; *AIDS Res Hum Retroviruses.* 8(5):613-23, 1992), and tumoricidal activity (*Nature* 330(6144):173-6, 1987; *J. Clin. Oncol.* 13(9):2342-53, 1995; *J Immunol.* 161(7):3536-42, 1998.

It has been suggested that AS101, as well as other tellurium-containing immunomodulators, stimulate the innate and acquired arm of the immune response. For example, it has been shown that AS101 is a potent activator of interferon (IFN) (IFN) in mice (*J. Natl. Cancer Inst.* 88(18):1276-84, 1996) and humans (*Nat. Immun. Cell Growth Regul.* 9(3):182-90, 1990; *Immunology* 70(4):473-7, 1990; *J. Natl. Cancer Inst.* 88(18):1276-84, 1996.)

It has also been demonstrated that AS101, as well as other tellurium-containing immunomodulators, induce the secretion of a spectrum of cytokines, such as IL-1, IL-6 and TNF-α, and that macrophages are one main target for AS101 (*Exp. Hematol.* 23(13):1358-66, 1995) and it was found to inhibit IL-10 at the m-RNA level, and this inhibition may cause an increase in IL-12 (Cell Immunol. 176(2):180-5, 1997); *J. Natl. Cancer Inst.* 88(18):1276-84, 1996).

Other publications describing the immunomodulation properties of AS101 include, for example, "The immunomodulator AS101 restores T(H1) type of response suppressed by Babesia rodhaini in BALB/c mice". *Cell Immunol* 1998 February; "Predominance of TH1 response in tumor-bearing mice and cancer patients treated with AS101". *J Natl Cancer Inst* 1996 September; "AS-101: a modulator of in vitro T-cell proliferation". *Anticancer Drugs* 1993 June; "The immunomodulator AS101 administered orally as a chemoprotective and radioprotective agent". *Int J Immunopharmacol* 1992 May; "Inhibition of the reverse transcriptase activity and replication of human immunodeficiency virus type 1 by AS 101 in vitro". *AIDS Res Hum Retroviruses* 1992 May; "Immunomodulatory effects of AS101 on interleukin-2 production and T-lymphocyte function of lymphocytes treated with psoralens and ultraviolet A". *Photodermatol Photoimmunol Photomed* 1992 February; "Use and mechanism of action of AS101 in protecting bone marrow colony forming units-granulocyte-macrophage following purging with ASTA-Z 7557". *Cancer Res* 1991 Oct. 15; "The effect of the immunomodulator agent AS101 on interleukin-2 production in systemic lupus erythematosus (SLE) induced in mice by a pathogenic anti-DNA antibody". *Clin Exp Immunol* 1990 March; "Toxicity study in rats of a tellurium based immunomodulating drug, AS-101: a potential drug for AIDS and cancer patients". *Arch Toxicol* 1989; "The biological activity and immunotherapeutic properties of AS-101, a synthetic organotellurium compound". *Nat Immun Cell Growth Regul* 1988; and "A new immunomodulating compound (AS-101) with potential therapeutic application". *Nature* 1987 November.

In addition to its immunomodulatory effect, AS101 is also characterized by low toxicity. Toxicity tests have shown that LD50 values in rats following intravenous and intramuscular administration of AS101 are 500-1000 folds higher than the immunologically effective dose.

While the immunomodulating effect of tellurium-containing compounds was studied with respect to various aspects thereof, the use of tellurium compounds in the treatment and prevention of neurodegenerative processes has never been suggested nor practiced hitherto.

SUMMARY OF THE INVENTION

The present invention successfully addresses the shortcomings of the presently known methods for the prevention or treatment of neurodegenerative diseases and processes by providing methods and compositions comprising tellurium compounds, which are devoid of the side effects of the commonly known methods.

The term "neurodegenerative process" as used herein refers to an abnormality in a mammal in which neuronal physical and/or functional integrity is threatened. Neuronal integrity can be threatened when neuronal cells display decreased survival or when the neurons can no longer propagate a signal. Examples of neurodegenerative processes include stroke syndromes, subarachnoid hemorrhage, brain dysfunction post-brain surgery, disorders of the nervous system due to hypoxia, hypoglycemia, brain or spinal damage, intoxication with drugs or gases, administration of chemotherapy, alcohol and the like and due to neurodegenerative disorders and other diseases or syndromes, such as, for example, Alzheimer's disease, amyotrophic lateral sclerosis, Parkinson's disease, myasthenia gravis, HIV-related encephalitis, cervical spondylosis, multiple sclerosis, Down's syndrome, and Huntington's chorea.

A key to curing these diseases is control of neuronal death including apoptosis. The tellurium compounds of the present invention may be administered systemically to one who is afflicted with neurodegenerative diseases or to patients who are believed to be susceptible to such diseases.

According to one aspect of the present invention there is provided a method for treating and preventing a neurodegenerative process in a subject in need thereof, the method comprising administering to the subject a therapeutically effective amount of at least one tellurium-containing compound.

According to another aspect of the present invention there is provided the use of at least one tellurium-containing compound in the preparation of a medicament for treatment or prevention of a neurodegenerative process.

According to yet another aspect of the present invention there is provided a pharmaceutical composition identified for use in the treatment or prevention of a neurodegenerative process.

According to further features in preferred embodiments of the invention described below, the neurodegenerative process which may be treated or prevented by the methods and compositions of the present invention include, without limitation, stroke syndromes, subarachnoid hemorrhage, brain dysfunction post-brain surgery, and disorders of the nervous system (such as, for example, hypoxia, hypoglycemia, central nervous system trauma (such as brain injury and spinal cord injury), intoxication by drugs or gases, administration of chemotherapy, alcohol abuse, and neurodegenerative disease (such as, for example, Alzheimer's disease, amyotrophic lateral sclerosis, Parkinson's disease, myasthenia gravis, HIV-related encephalitis, cervical spondylosis, multiple sclerosis, Down's syndrome, and Huntington's chorea).

According to further features in preferred embodiments of the invention described below, the tellurium-containing compound of the present invention is a compound comprising at least one tellurium dioxide moiety and optionally and preferably is at least one of tellurium dioxide (TeO$_2$) per se, an organic complex of TeO$_2$ (as detailed hereinbelow), a compound having general Formula I:

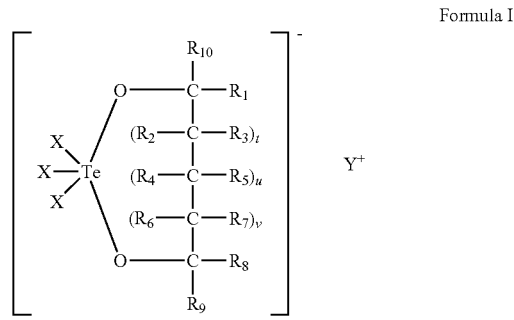

Formula I a compound having general Formula II:

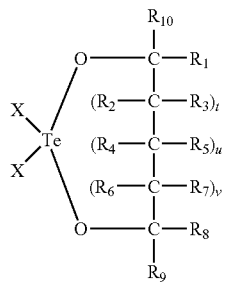

Formula II and a compound having general Formula III:

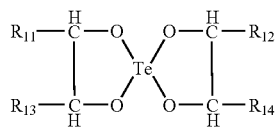

Formula III wherein:
each of t, u and v is independently 0 or 1;
each of m and n is independently an integer from 0 to 3;
Y is selected from the group consisting of ammonium, phsophonium, potassium, sodium and lithium;
X is a halogen atom; and
each of $R_1$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

Preferably, the tellurium-containing compound has general Formula I.

According to an embodiment in which the tellurium-containing compound has general Formula I, preferably t, u and v are each 0. More preferably, each of $R_1$, $R_8$, $R_9$ and $R_{10}$ is hydrogen; more preferably X is a halogen atom, most preferably the halogen atom is chloro. More preferably, Y is ammonium. The preferred compound according to this embodiment is referred to hereinafter as AS101.

According to further features in the described preferred embodiments of the present invention, wherein the neurodegenerative process is due to spinal cord injury, the tellurium-containing compound is preferably administered for a period of up to 21 days following the injury, more preferably for a period of up to 7 days following injury. Administration may be effected, for example, by the oral, parenteral, rectal, nasal or inhalation routes. Preferably, administration is effected either orally or parenterally. More preferably, administration is effected by cerebro-vascular injection.

According to still further features in the described preferred embodiments of the methods of the present invention, administering is effected systemically. Preferably, for systemic administration, a therapeutically effective amount of a tellurium-containing compound (e.g., a compound of formula I, II or III) ranges from about 0.1 mg/m²/day to about 20 mg/m²/day, more preferably from about 1 mg/m²/day to about 10 mg/m²/day, and more preferably the therapeutically effective amount is about 3 mg/m²/day.

According to still further features in the described preferred embodiments of the methods or compositions of the present invention, the tellurium-containing compound forms a part of a pharmaceutical composition, further comprising a pharmaceutically acceptable carrier. Preferably, a concentration of tellurium-containing compound of formula I, II or III in the carrier ranges from about 0.01 weight percent to about 50 weight percents, more preferably from about 0.1 weight percent to about 25 weight percents, of the total weight of the composition.

According to still further features in the described preferred embodiments of the methods or compositions of the present invention, the pharmaceutical composition may optionally further comprise at least one additional active agent. The additional active agent may comprise, for example, a neurotropic growth factor, an antispasticity agent, and an anti-inflammatory agent, a beta-adrenergic blocking agent and brimonidine. Examples of suitable additional active agents for use in the compositions of the present invention include, without limitation, methylprednisolone, Naloxone, Tirilazad, basic fibroblast growth factor, epithelial growth factor, insulin-like growth factor, brain-derived neurotrophic factor, interferon and glial-derived neurotrophic factor.

As used herein, the term "about" refers to ±10%.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "therapeutically effective amount" or "pharmaceutically effective amount" denotes that dose of an active ingredient or a composition comprising the active ingredient that will provide the therapeutic effect for which the active ingredient is indicated.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS:

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows activation of $p21^{ras}$ by GDP/GTP exchange. AS101 (ammonium trichloro(dioxoethylene-O,O')tellurate) was incubated with recombinant $p21^{ras}$ for 10 minutes;

FIG. 2 shows activation of ERK1/ERK2 by AS101 using myelin basic protein as substrate. NIH3T3 cells were incubated with AS101 for 10 minutes with or without farnesyl transferase inhibitor. FIG. 3 shows that treatment of PC12 cells with AS101 induced neuronal differentiation in a dose-dependent manner;

FIG. 3a shows AS101 induced neuronal differentiation in PC12 cells;

FIG. 3b shows that treatment with AS101 of PC12 cells expressing the dominant negative form (N17) of ras did not induce neuronal differentiation;

FIG. 3c shows that treatment of with AS101 of PC12 cells expressing a point mutation in CSY118 of P21ras did not result in neuronal differentiation;

FIG. 4 shows that in cells incubated with AS101 for 15 minutes, AS101 can activate p21 ras downstream effector molecules c-raf-1;

FIG. 5 shows that in cells incubated with AS101 for 24 hours, AS101 results in a pronounced increase in p21waf protein expression in a dose dependent manner;

DETAILED DESCRIPTION OF THE INVENTION

Figure 6:
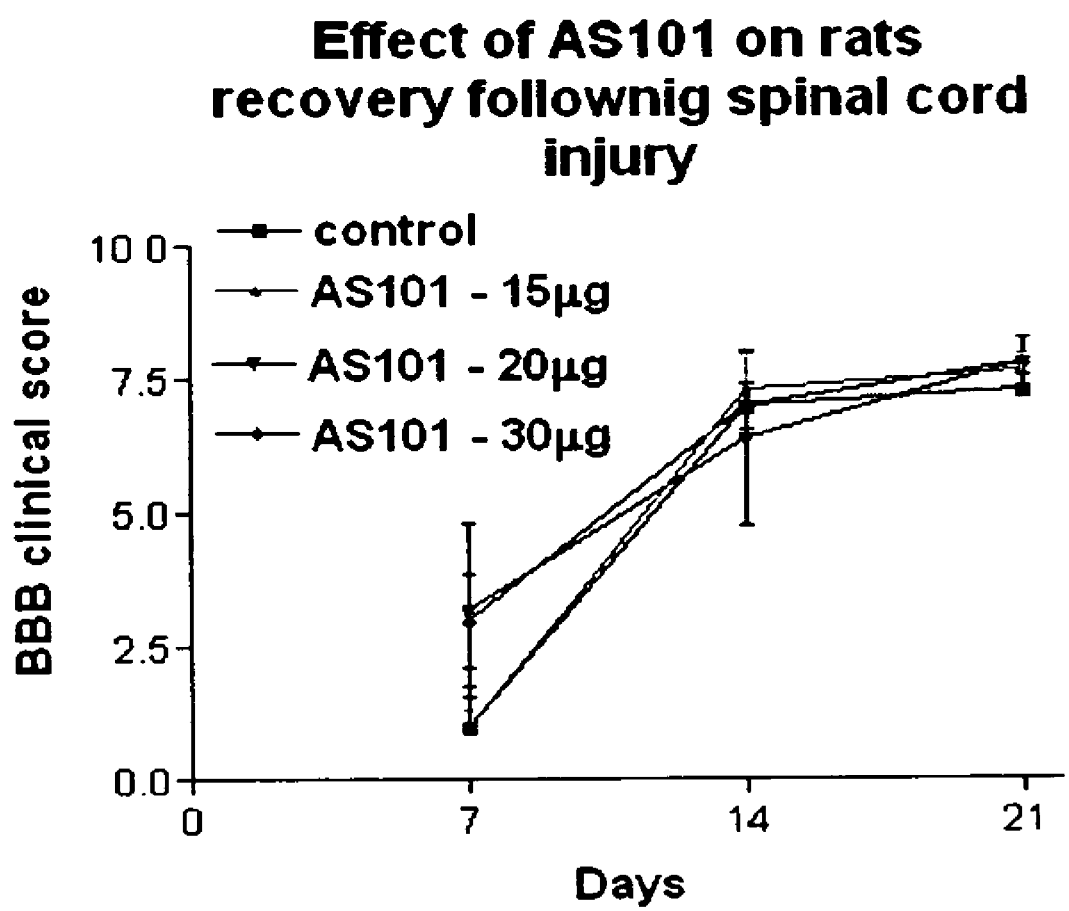
FIG. 6 is a plot showing the effect of AS101 on recovery of rats following spinal cord injury, as assessed by Basso, Beattie and Bresnahan (BBB) locomotor scale score.

The present invention is of methods and compositions comprising tellurium-containing compounds for treatment and prevention of neurodegenerative processes and diseases, such as those caused by trauma.

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The demonstration that neuronal death can be blocked by manipulation of the cell death program, regardless of the cell death signal, has raised enormous hopes for the treatment of neurodegenerative diseases in which the cell death signals are of unknown origin or have already occurred. In recent years apoptosis has been described in a variety of human neurodegenerative disorders, primarily based on the detection of neuronal nuclei with apparent DNA cleavage in post-mortem brain tissue. Such nuclei definitive evidence in support of apoptosis are the electron microscopic findings of nuclear chromatin condensation in the substrantia nigra pars compacta (SNC) of PD brains.

Critical observations have been made by Tatton and Olanow suggesting that in neurodegenerative disorders, degenerating nerve cells may be in a pre-apoptotic state for some time before entering the end stages of apoptosis, as marked by chromatin condensation and DNA cleavage. Thus, neurodegenerative disorders might reflect accelerated apoptosis as a result of agonal events in neurons that were pre-apoptotic and committed to undergo apoptosis at a later time point. This observation provides an opportunity to interfere with the cell death process and to design a putative neuroprotective agent.

While conceiving the present invention, it was envisioned that since AS101 is a potent modulator of the immune response, and is involved in apoptosis, and since AS101 is further characterized as a substantially non-toxic agent, AS101, as well as other tellurium compounds of this family, could serve as potent therapeutic agents for neuroprotection against neurodegenerative processes associated with trauma, devoid of the disadvantages associated with the presently known agents for treating these conditions described hereinabove.

As used herein, the phrase "tellurium-containing compound" encompasses any compound that includes one or more tellurium atoms and exhibits immunomodulating properties. Preferably, the tellurium-containing compound includes at least one tellurium dioxide moiety.

The phrase "immunomodulating properties" includes any effect of the compound on the immune response of a subject. Exemplary immunomodulating properties can be manifested, for example, by an effect on cytokines secretion, interleukins production, lymphocytes function, and the like.

In attempting to elucidate the cellular mechanisms of the effects of AS101, it was observed that the primary cellular target of AS101 is the small G-protein p21 ras. AS101 directly binds to recombinant p21 ras and activates it via GDP/GTP exchange (see FIG. 1). In a cellular model of Jurkat T cells or NIH3T3 cells, AS101 activated ras and its downstream effector, Erk. This was shown by the kinase assay of immunoprecipitated Erk using myelin basic protein as substrate (see FIG. 2). Moreover, the ability of AS101 to activate the ras/raf/ere pathway in B16 melanoma cells has recently been shown. This property was found necessary for the ability of AS101 ability to cause G0/G1 cell cycle arrest.

Based on these signaling properties, and the role of ras/erk in the survival and differentiation of PC12 cells, this cell line was utilized for studying the differentiating ability of AS101 and its potential ability to prevent apoptotic death caused by loss of trophic support, as described in the Examples presented hereinbelow.

Treatment of PC12 cells with AS101 induced neuronal differentiation in a dose-dependent manner (see FIG. 3). The optimal doses were found to be 0.5 and 1 µg/ml. Morphological changes appeared in AS101-treated cells, which included membrane ruffling, flattening of cells, enlarged cell bodies, and the formation of stable neurites. The morphological appearance of AS101 treated cells did not differ from that of NGF treated cells. Treatment with AS101 of PC12 cells expressing the dominant negative form (N17) of ras did not result in their differentiation, thus implicating ras as a crucial signaling molecule in the differentiating ability of AS101. Moreover, treatment with AS101 of PC12 cells expressing a point mutation of Cys118 of P21ras did not result in cellular differentiation while it did not prevent this activity by NGF, suggesting Cys118 as the target of AS101 in the p21ras molecule (FIG. 3).

It was further shown that AS101 could activate p21ras downstream effector molecules c-raf-1 (see FIG. 4). In view of the ability of AS101 to induce neuronal differentiation of PC12 cells, the effect of AS101 on the expression of p21waf, known to increase following differentiation of cells by NGF, was studied. Treatment of PC12 cells with AS101 for 24 h resulted in a pronounced increase in p21waf protein expressing in a dose-dependent manner. The effective concentrations of AS101 were similar to those inducing differentiation of PC12 cells (FIG. 5). Pretreatment of the cells with farnesyl transferase inhibitor, with geldanamycin (which pharmacologically depletes c-raf-1), or with PD98059 (a MEK inhibitor) abolished p21waf protein expression induced by AS101. These results imply that p21waf protein expression induced by AS101 is both ras, c-raf-1, and MAPK-dependent.

Based on the ability of AS101 to activate the ras/erk pathway and to upregulate p21waf, which effects have been shown to mediate the survival of PC12 cells, the ability of AS101 to prevent apoptotic cell death of differentiated PC12 cells following withdrawal of trophic support was studied. As shown in Tables 1 and 2, treatment of PC12 cells with AS101 resulted in the induction of G1 arrest in a dose-dependent manner. Following incubation of the cells with AS101 for 24 hours, 68.1% of the cells stimulated with 0.5 µg/ml AS101 accumulated in G1 as compared to 33% of untreated cells. More importantly, treatment of PC12 cells with anti-NGF abs 5 days following incubation of the cells with NGF, resulted in 50% apoptosis 24 hours later. Addition of 0.5 µg/ml AS101 with anti-NGF abs significantly decreased the rate of apoptosis occurring one day later, while it did not significantly differ from that of control cells incubated without AS101, and amounted to 34.9%. Table 1 below presents the results obtained for the effect of AS101 on apoptosis induced by NGF withdrawal in PC12 cells. Table 2 below presents the results obtained for the cell cycle analysis of AS101-treated PC12 Cells

TABLE 1

|  | Apoptotic |
| --- | --- |
| CONTROL | 6.3 |
| AS101 0.1 µg/ml | 8.8 |
| AS101 0.5 µg/ml | 5.3 |
| AS101 1 µg/ml | 6.6 |
| NGF | 5.9 |
| NGF + anti NGF Ab | 49.8 |
| NGF + anti NGF + Ab + AS101 | 5.8 |
| CONTROL + anti NGF Ab | 5.3 |

TABLE 2

|  | G0/G1 | S | G2/M |
| --- | --- | --- | --- |
| CONTROL | 33.9 | 44.9 | 21.2 |
| AS101 0.1 µg/ml | 39.7 | 43.9 | 16.4 |
| AS101 0.5 µg/ml | 68.1 | 4.0 | 27.9 |
| AS101 1 µg/ml | 67.5 | 3.5 | 29 |
| NGF | 65.2 | 7.3 | 27.5 |
| NGF + anti NGF Ab | 46.3 | 12.2 | 41.6 |
| NGF + anti NGF + Ab + AS101 | 68 | 4.4 | 27.6 |
| CONTROL + anti NGF Ab | 34.9 | 42.3 | 22.7 |

Figure 7:
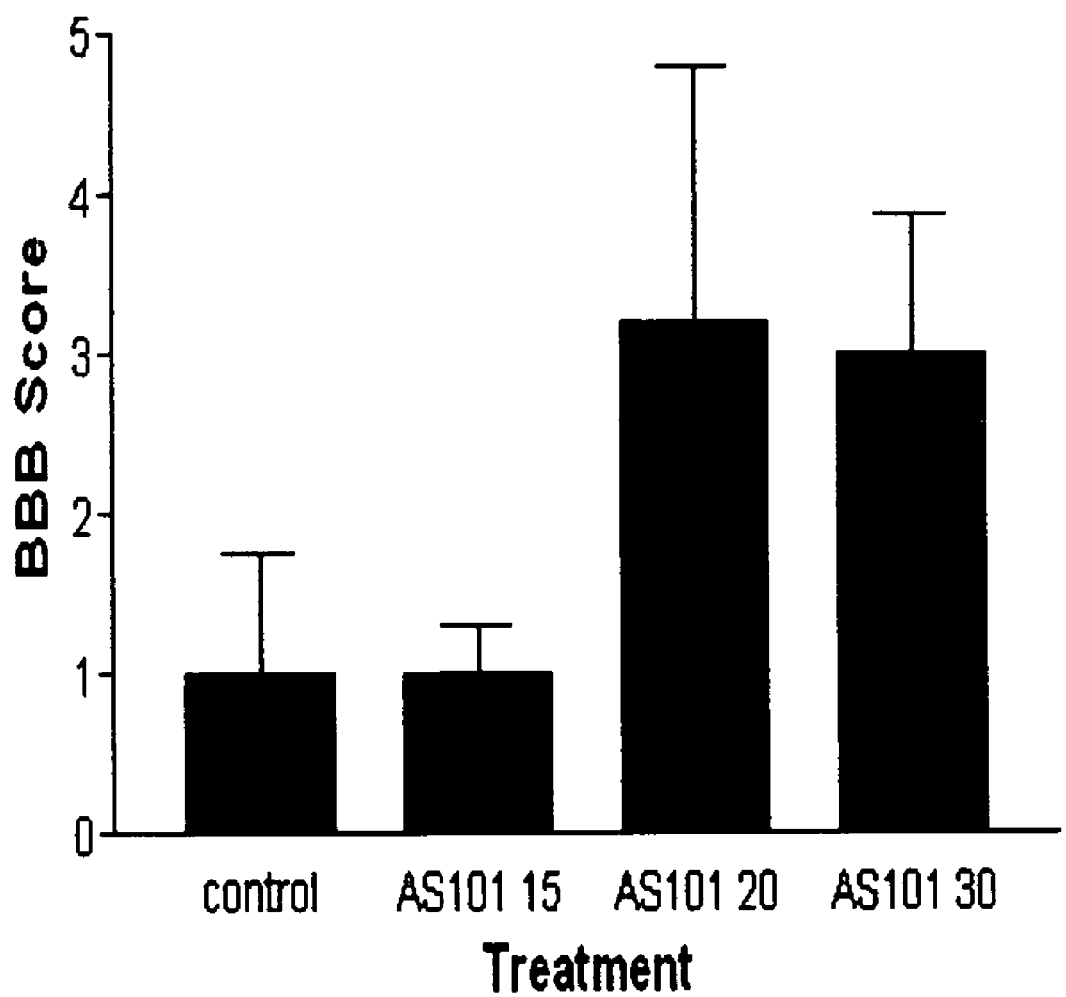
FIG. 7 is a bar graph showing BBB score one week following spinal cord injury as affected by various treatments.

As discussed in Example 6, and as shown in FIGS. 6 and 7, studies evaluating the therapeutic effect of AS101 using a rat spinal cord injury model demonstrated that partial functional recovery was seen with administration of AS101, as assessed by the Basso, Beattie and Bresnahan (BBB) locomotor scale score. Spinal cord injury was demonstrated in all treated animals. Repeated administration of AS101 improved functional recovery (1±1.7 vs 3±2 control high dose respectively) in a dose-dependent manner. Furthermore, there was no mortality in the 20 and 30 µg AS101 treated groups, in comparison with two deaths observed in the control group and one in the low dose group. Administration of AS101 was well tolerated, and was not accompanied by observed adverse side effects.

Figure 8:
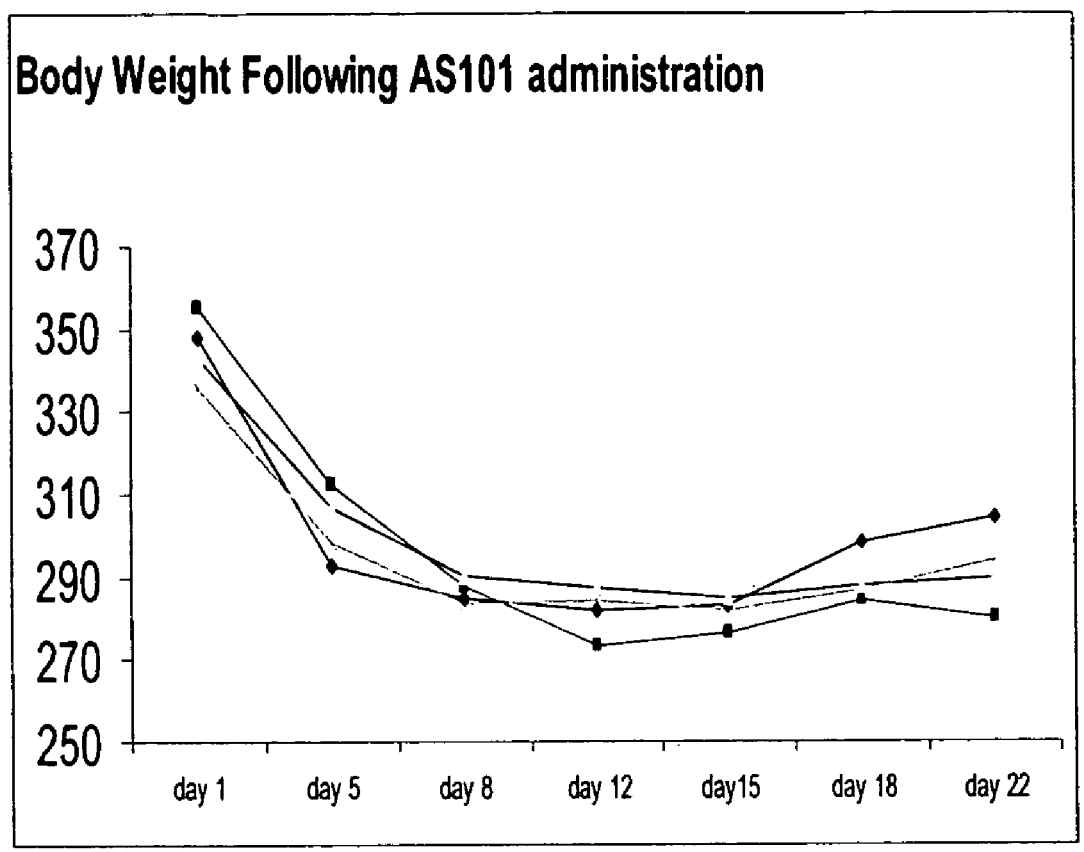
FIG. 8 is a plot showing changes in body weight following AS101 administration after spinal cord injury.
Figure 9:
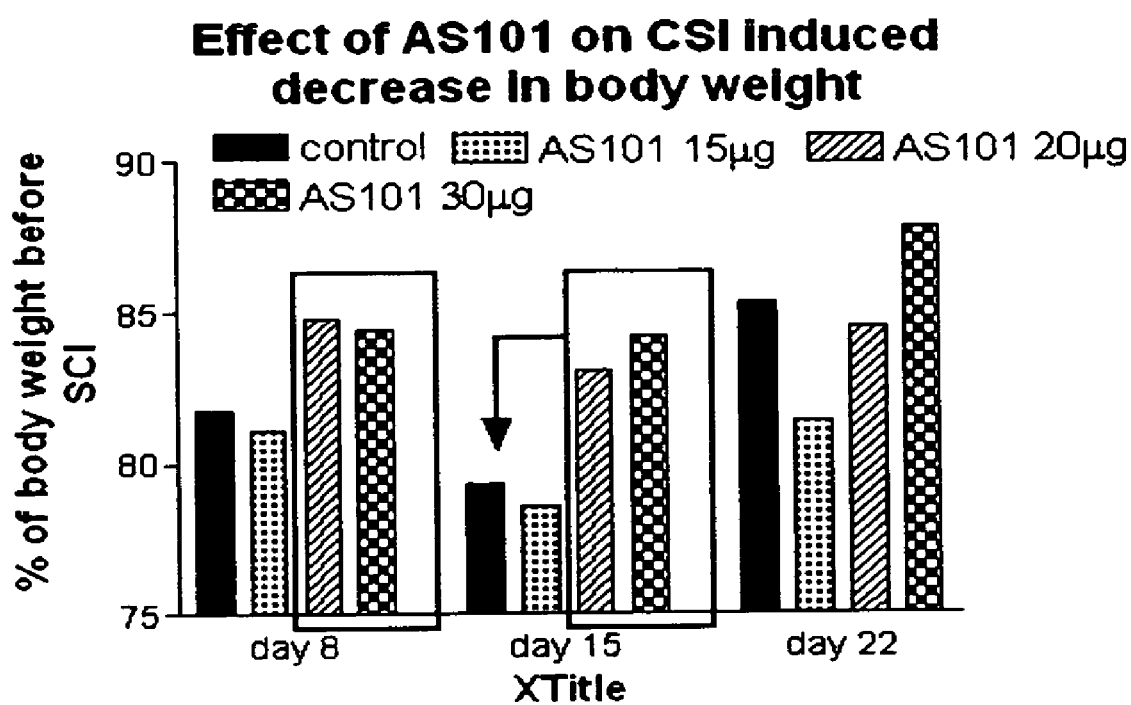
FIG. 9 is a bar graph showing the effect of AS101 on spinal cord injury-induced decrease in body weight.

As a non-specific marker for recovery, in addition to clinical signs, changes in body weight were recorded. As shown in FIGS. 8 and 9, reduction in body weight following injury was attenuated by administration of AS101.

The results show that during the first week of drug administration following spinal cord injury, AS101 seems to provide therapeutic benefits. This is shown by: (a) the BBB test results (b) reduced mortality (c) relative changes in body weight.

During the second and third weeks of treatment, no beneficial effect of AS101 was observed. AS101 is an immunomodulator with pro-inflammatory properties. Previously, it has been reported that the acute response to spinal cord injury involves alterations in genes responsible for inflammation, cell cycle alteration, and altered receptor function. In contrast, the delayed response includes changes in the expression of HSP27, MAG, MAP-2, IGF-1 and ApoE. In different spinal cord injury and neurodegenerative models, modulation of inflammatory processes throughout different stages of the pathology has different responses. Therefore, while immunomodulation can attenuate damage early following the insult, immunomodulation at a latter stage, can hamper protective/regenerative processes, being modulated by different protein-targets, and thus, diminishing the overall therapeutic benefit as a result of the acute drug administration.

The tellurium-containing compounds utilized according to the present invention preferably have one or more tellurium dioxide moiety and thus can be, for example, an inorganic tellurium-containing compound such as, for example, tellurium dioxide ($TeO_2$) per se, halogenated tellurium, sulfonated tellurium, phsophorylated tellurium, as well as salts thereof (e.g., ammonium salts, alkaline salts, phosphonium salts and the like) and any complexes thereof.

The compound can alternatively be an organic tellurium-containing compound which includes one or more tellurium atoms and one or more organic moieties that are attached thereto.

Representative examples of inorganic tellurium-containing compounds that were shown to exert immunomodulating properties and hence are particularly useful in the context of the present invention include, for example, $TeO_2$ per se. Also included are compounds that form $TeO_2$ in aqueous solutions, preferably in the form of an organic complex such as, for example, a $TeO_2$ complex with citric acid or ethylene glycol. A representative example of the latter is the complex $TeO_2 \cdot HOCH_2CH_2OH \cdot NH_4Cl$.

Organic tellurium-containing compounds that were shown to exert immunomodulating properties and hence are particularly useful in the context of the present invention include, for example, ammonium salts, or any other salts, of halogenated tellurium-containing compounds having a bidentate cyclic moiety attached to the tellurium atom. The bidentate cyclic moiety is preferably a di-oxo moiety having two oxygen atoms attached to the tellurium atom. Alternatively, the bidentate cyclic moiety can be a di-thio moiety, in which two sulfur atoms are attached to the tellurium atom.

Preferred compounds in this category are collectively represented by the general Formula I:

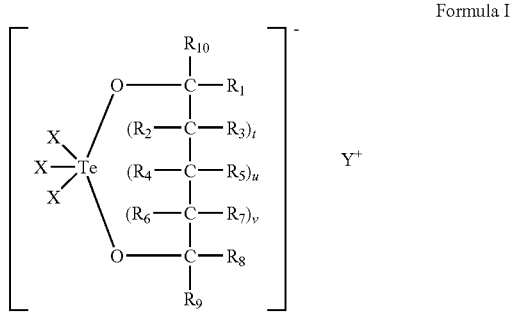

Formula I

In the general Formula I above, each of t, u and v is independently 0 or 1, such that the compound may include a five-membered ring, a six-membered ring, or a seven-membered ring o. Preferably, each of t, u and v is 0, such that the compound includes a five-membered ring.

X is a halogen atom, as described hereinabove, and is preferably chloro.

Y is selected from the group consisting of ammonium, phsophonium, potassium, sodium and lithium, and is preferably ammonium.

Each of $R_1$-$R_{10}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "haloalkyl" refers to an alkyl, as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, —$CH_2CONH_2$; —$CH_2CH_2CONH_2$; —$CH_2CH_2CH_2CONH_2$ and the like.

The term "cyanoalkyl" refers to an alkyl, as this term is defined herein, substituted by an cyano group, as defined herein, and includes, for example, —$CH_2CN$; —$CH_2CH_2CN$; —$CH_2CH_2CH_2CN$ and the like.

The term "N-monoalkylamidoalkyl" refers to an alkyl, as this term is defined herein, substituted by an amide group, as defined herein, in which one of R' and R" is an alkyl, and includes, for example, —$CH_2CH_2CONHCH_3$, and —$CH$—$_2$ $CONHCH_2CH_3$.

The term N,N-dialkylamidoalkyl refers to an alkyl, as this term is defined herein, substituted by an amide group, as defined herein, in which both R' and R" are alkyl, and includes, for example, —$CH_2CON(CH_3)_2$; $CH_2CH_2CON(CH_2$—$CH_3)_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, phosphonyl, phosphinyl, carbonyl, thiocarbonyl, carboxy, thiocarboxy, carbamate, thiocarbamate, amido, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "carboxy" group refers to a +C(=O)—O—R' or a —O—C(=O)—R' group, where R' is as defined herein.

A "sulfinyl" group refers to an —S(=O)—R' group, where R' is as defined herein.

A "sulfonyl" group refers to an —S(=O)$_2$—R' group, where R' is as defined herein.

A "sulfate" group refers to a —O—S(=O)$_2$—OR' group, where R' is as defined herein.

A "sulfonamido" group refers to a —S(=O)$_2$—NR'R" group or a R'S(=O)$_2$—NR", with R' is as defined herein and R" is as defined for R'.

A "carbamyl" or "carbamate" group refers to an —OC(=O)—NR'R" group or a R"OC(=O)—NR'— group, where R' and R" are as defined herein.

A "thiocarbamyl" or "thiocarbamate" group refers to an —OC(=S)—NR'R" group or an R"OC(=S)NR'-group, where R' and R" are as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

A "nitro" group refers to an —NO$_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

As cited hereinabove, the compounds in this category are salts of organic tellurium-containing compounds. The salts can be, for example, ammonium salts, phsophonium salts and alkaline salts such as potassium salts, sodium salts, lithium salts and the like.

Hence, Y in Formula I above can be a phosphonium group, as defined herein, an ammonium group, as defined herein, potassium ($K^+$), sodium ($Na^+$) or lithium ($Li^+$).

As used herein, the term "phosphonium" describes a —P$^+$R'R"R'" group, with R' and R" as defined herein and R'" is as defined for R'. The term "phsophonium", as used herein, further refers to a —P$^+$R$_6$ group, wherein each of the six R substituents is independently as defined herein for R, R" and R'".

The term "ammonium" describes a —N$^+$R'R"R'" group, with R', R" and R'" as defined herein.

More preferred compounds in this category include compounds having the general Formula I described above, in which Y is ammonium or phosphonium, t, u and v are each 0, and each of $R_1$, $R_8$, $R_9$ and $R_{10}$ is independently hydrogen or alkyl. These compounds can be represented by the following structure:

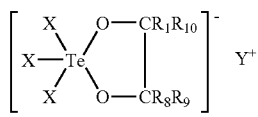

wherein each of $R_1$, $R_8$, $R_9$ and $R_{10}$ is independently hydrogen or alkyl, preferably methyl, and X is halogen, preferably chloro.

The presently most preferred compound for use in the context of the present invention has the following structure:

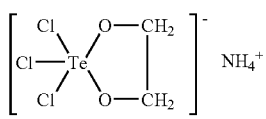

This compound is ammonium trichloro(dioxyethylene-O, O')tellurate, which is also referred to herein and in the art as AS101.

Additional representative examples of organic tellurium-containing compound that are suitable for use in the context of the present invention include halogenated tellurium having a bidentate cyclic moiety attached to the tellurium atom. The bidentate cyclic moiety is preferably a di-oxo ligand having two oxygen atoms attached to the tellurium atom. Alternatively, the bidentate cyclic moiety can be a di-thio ligand, in which two sulfur atoms are attached to the tellurium atom.

Preferred compounds in this category can be represented by the general Formula II:

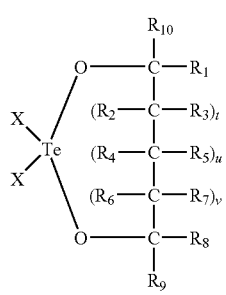

wherein t, u, v, X and $R_1$-$R_{10}$ are as defined hereinabove.

More preferred compounds are those in which t, u, and v are each 0, and X is chloro, such as, but not limited to, the compound having the following structure:

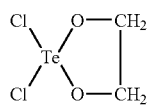

The above compound is also known and referred to herein as AS103.

The organic tellurium-containing compounds having Formulae I and II can be readily prepared by reacting tetrahalo-telluride such as $TeCl_4$ with a dihydroxy compound, as is described in detail in U.S. Pat. Nos. 4,752,614, 4,761,490, 4,764,461 and 4,929,739, which are incorporated by reference as if fully set forth herein.

Additional representative examples of organic tellurium-containing compounds that are suitable for use in the context of the present invention include compounds in which two bidentate cyclic moieties are attached to the tellurium atom.

Preferably, each of the cyclic moieties is a di-oxo moiety. Alternatively, one or more of the cyclic moieties is a di-thio moiety.

Preferred compounds in this category are collectively represented by the general Formula III:

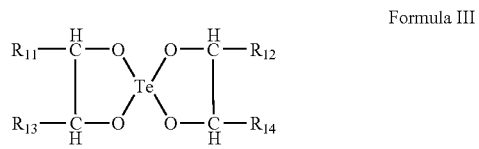

Formula III wherein each of $R_{11}$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfmyl, sulfate, amine, aryl, heteroaryl, phosphate, phosphonate and sulfoneamido, as these terms are defined herein.

The most preferred compound in this category is a compound in which each of $R_{11}$-$R_{14}$ is hydrogen. This compound is also known as AS102.

Additional organic tellurium-containing compounds that are suitable for use in the context of the present invention include those having the general Formula V:

Formula V wherein each of Ra, Rb, Rc and Rd is independently selected from the group consisiting of halogen alkyl, aryl, cycloalkyl, alkoxy, aryloxy, thioalkoxy, thioaryloxy, carboxy, carbonyl, thiocarboxy, thiocarbonyl, carbamyl, and thiocarbamyl, as these terms are defined hereinabove, whereby at least one of Ra-Rd is not halogen, namely, is selected from the group consisiting of alkyl, aryl, cycloalkyl, alkoxy, aryloxy, thioalkoxy, thioaryloxy, carboxy, carbonyl, thiocarboxy, thiocarbonyl, carbamyl, and thiocarbamyl.

Compounds in this category include those in which one of Ra, Rb, Rc and Rd is halogen alkyl, aryl, cycloalkyl, alkoxy, aryloxy, thioalkoxy, thioaryloxy, carboxy, carbonyl, thiocarboxy, thiocarbonyl, carbamyl, or thiocarbamyl, whereby the others are halogen atoms, e.g., chloro.

Other compounds in this category include those in which two or three of Ra, Rb, Rc and Rd are as described above and the others are halogens e.g., chloro.

Other compounds in this category include those in which each of Ra, Rb, Rc and Rd is as described hereinabove.

The compounds described above can be administered or otherwise utilized in this and other aspects of the present invention, either as is or as a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

In any of the different embodiments of the method of the present invention, the tellurium-containing compounds described herein can be provided to a subject either per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutically acceptable carriers or diluents may be, for example, binders, (e.g., syrup, gum Arabic, gelatin, sorbitol, tragacanth, polyvinylpyrrolidone, etc), excipients (e.g., lactose, sucrose, corn starch, sorbitol), lubricants (e.g., magnesium stearate, talc, polyethylene glycol, silica, etc.), disintegrants (e.g. microcrystalline cellulose, potato starch, etc.), wetting agents (e.g. sodium lauryl sulfate, etc.), and the like. These pharmaceutical preparations may be in the form of a solid preparation such as tablets, capsules, powders, etc., or in the form of a liquid preparation such as solution, suspension, emulsion, etc., when administered orally. When administered parenterally, the pharmaceutical preparations may be in the form of a suppository, an injection or an intravenous drip, a physiological salt solution, and so on.

Preferably, a concentration of tellurium-containing compound of formula I, II or III in the carrier ranges from about 0.01 weight percent to about 50 weight percents, more preferably from about 0.1 weight percents to about 25 weight percents, of the total weight of the composition.

Therapeutic application of AS101 and other tellurium compounds, can be contemplated to be accomplished by any suitable therapeutic method and technique presently or prospectively known to those skilled in the art. The tellurium compound may be administered in a variety of forms. These include orally, parenterally, rectally, nasally, topically or via inhalation. The parenteral route of administration may be intravenous, subcutaneous, intramuscular, etc. The compounds may also be administered directly to the location of the dopaminergic neurons to be protected, i.e. directly to the brain or cerebrospinal fluid by cerebro-ventricular injection, by injection in to the cerebral parenchyma or through a surgically inserted shunt into the lateral cerebro ventricle of the brain.

In general, the composition of the subject invention will be formulated such that an effective amount of bioactive tellurium compound is combined with a suitable carrier in order to facilitate effective administration of the composition. The oral administration may be as a solid dosage form i.e. tablet with conventional excipients such as lactose, microcrystalline cellulose and the like.

It has been found that the tellurium compounds useful in the practice of the invention will hydrolyze in the presence of water. These hydrolyzed compositions are active in vivo and in vitro although the hydrolyzed compositions eventually decompose. For this reason, the compositions should be freshly prepared or administered orally in the dry form. Preferably, the compounds should be kept under anhydrous conditions until just prior to being used.

The tellurium compound is administered in a therapeutically effective amount. The term "therapeutically effective amount" or "pharmaceutically effective amount" denotes that dose of an active ingredient or a composition comprising the active ingredient that will provide the therapeutic effect for which the active ingredient is indicated. Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The exact formulation, route of administration and dosage can be chosen by the individual physician in view of the patient's condition. [See e.g., Fingl, et al., (1975) "The Pharmacological Basis of Therapeutics", Ch. 1 p. 1].

Dosages can be titrated to the individual patient. The dose of ammonium trichloro (dioxoethylene-O,O') tellurate or a pharmaceutically acceptable salt thereof varies depending on the exact formulation, route of administration, ages, weights and condition of individual patients, or the severity of the disease, but in humans it may be in the range of from about 0.1 to about 10 mg/m$^2$, preferably in the range of from about 2 to about 4 mg/m$^2$, and most preferably 3 mg/m$^2$ administered on alternate days or daily in one or more divided doses.

When administering systemically, a therapeutically effective amount of the tellurium-containing compounds described herein may range, for example, from about 0.1 mg/m$^2$/day to about 20 mg/m$^2$/day and thus can be for example, 0.01 mg/m$^2$/day, 0.02 mg/m$^2$/day, 0.03 mg/m$^2$/day, 0.04 mg/m$^2$/day, 0.05 mg/m$^2$/day, 0.1 mg/m$^2$/day, 0.5 mg/m$^2$/day, 1 mg/m$^2$/day, 3 mg/m$^2$/day, 5 mg/m$^2$/day, 10 mg/m$^2$/day, and up to 20 mg/m$^2$/day. Preferably, for systemic administration, a therapeutically effective amount of a compound of formula I, II or III ranges from about 0.1 mg/m$^2$/day to about 10 mg/m$^2$/day.

Preferably, when administered parenterally, the therapeutically effective amount is 0.01 mg/m$^2$/day and higher and thus can be, for example, 0.01 mg/m$^2$/day, 0.05 mg/m$^2$/day, 0.1 mg/m$^2$/day, 0.2 mg/m$^2$/day, 0.5 mg/m$^2$/day, 0.6 mg/m$^2$/day, 0.7 mg/m$^2$/day, 0.8 mg/m$^2$/day, 0.9 mg/m$^2$/day, 1 mg/m$^2$/day, 2 mg/m$^2$/day, 3 mg/m$^2$/day, 4. mg/m$^2$/day, 5 mg/m$^2$/day, and up to 20.0 mg/m$^2$/day.

Depending on the severity and responsiveness of the condition to be treated, dosing can be of a single or a plurality of administrations, with course of treatment lasting from several days to several weeks or until cure is effected or diminution of the disease state is achieved. Preferably, when the condition is caused by spinal cord injury, administration of the compositions of the present invention is effected for up to 21 days, more preferably up to 7 days.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The amount of a composition to be administered will, of course, be dependent on the subject being treated, the severity of the affliction, the manner of administration, the judgment of the prescribing physician, etc.

One or more of the tellurium compounds of the present invention may be employed alone, as the sole active agent(s), or in combination with a second active ingredient comprising, for example, a neuroprotective compound known in the art.

The method according to this aspect of the present invention can further comprise, in addition to administering the tellurium-containing compounds described above, co-administration of an additional active agent. The co-administration can be effected prior to, concomitant with or subsequent to the administration of the tellurium-containing compound. The additional active agent is used for providing an additive beneficial effect in terms of the ailment being treated, conditions associated with the ailment being treated or other parameters such as psychological effects and prophylactic effects.

Hence, exemplary additional active agents according to this embodiment of present invention include, without limitation, one or more, or any combination of an antibiotic agent, an antimicrobial agent, an anesthetic agent, a suitable antioxidant, a chemotherapeutic agent, an antidepressant, an antihistamine, a vitamin, and a hormone.

The treatment and prevention of neurodegenerative processes according to the present invention may be combined with other treatment methods known in the art (i.e., combination therapy). The tellurium-containing compounds described above can thus be, for example, co-administered (simultaneously or separately) with additional agents for treating degenerative diseases, including neurotrophic factors, (such as basic fibroblast growth factor, epithelial growth factor, insulin-like growth factor, brain-derived neurotrophic factor, and glial-derived neurotrophic factor), an antispasticity agent, an anti-inflammatory agent, an interferon, brimonidine and beta-adrenergic blocking agents.

Preferred examples of additional active agents include methylprednisolone, Naloxone, Tirilazad.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the pharmaceutically acceptable salts and esters of these agents.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox$^R$), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs"), corticotropin-releasing factor (CRF) antagonists, α-adrenoreceptor antagonists, NK1-receptor antagonists, 5-$HT_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Compositions including the preparation of the present invention formulated in a compatible pharmaceutical carrier may also be prepared and placed in an appropriate container. The compositions are preferably identified in print, in or on the packaging material, for use in the treatment or prevention of a neurodegenerative process associated with trauma.

The compositions of the present invention may be packed or presented in any convenient way. For example, they may be packed in a tube, a bottle, or a pressurized container, using techniques well known to those skilled in the art and as set forth in reference works such as Remington's Pharmaceutical Science 15$^{th}$ Ed. It is preferred that the packaging is done in such a way so as to minimize contact of the unused compositions with the environment, in order to minimize contamination of the compositions before and after the container is opened.

Compositions of the present invention may, if desired, be presented in a pack or dispenser device, such as an FDA approved kit, which may contain one or more unit dosage forms containing the active ingredient. The pack may, for example, comprise glass, plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Assessment of the Neuroprotective Effects of AS101

To assess the neuroprotective effects of AS101, PC12 cells were maintained in Dulbecco's modified Eagle's medium supplemented with 8% heat inactivated horse serum, 8% heat inactivated fetal bovine serum, glutamine (5 mM) and 50 µg/ml gentamycin at 37° C.

PC12 cells were washed in serum-free medium, resuspended to $1-5 \times 10^6$ cells/ml. After 24 hours of incubation at 37° C. in culture, the cells were supplemented with 3 ml of medium (RPMI 1640 containing 10% FCS, 2% glutamine and 1 mg/ml G418 (Life Technologies, Inc.). After another 24 hours, cells were resuspended and maintained in the selection medium. After 3-4 weeks in selective medium, transfected cells were analyzed for via Western blotting. Results are expressed as percent p21 as compared to the negative (no drug) control.

The ras Asn-17 gene was then cloned into a mammalian expression vector. Transfection of PC12 cells with the plasmid DNA was performed with the calcium phosphate precipitation technique as described previously.

PC12 cell extracts (20 µg/lane of protein) boiled under reducing conditions, were subjected to electrophoresis on 7.5 and 12.5% polyacrylamide gels and electro-transferred to nitrocellulose membranes. The membrane was blocked for one hour with 10% powdered milk in 0.2% Tween 20, Tris-buffered saline, and then incubated with the appropriate specific detecting antibodies. Immunoreactive proteins were detected with horseradish peroxidase-conjugated secondary antibodies (Amersham, Arlington Heights, Ill.) and a chemiluminescence reagent. For immunoprecipitation studies, immune complexes were precipitated with Protein A-Sepharose (Pharmacia) and, following electrophoresis, were blotted with anti-phosphoserine or anti-phosphotyrosine antibodies.

Endogenous JNK and erk were immunoprecipitated from cell lysates with specific antibodies and their activities measured by using $p^{32}$ ATP and glutathione s-transferase (GST) e-jun or myelin basic protein (MPB) respectively, as the substrate. Samples were run on SDS-polyacrylamide gel electrophoresis gels and subjected to PhosphorImager analysis.

Example 2

Activadon of the Ras Superfamily GTPases

The effect of AS101 on signaling pathways that are controlled by Ras superfamily GTPases was screened by parallel analysis of the activation of the Ras family GTPases and their effectors (FIG. 1). The primary methods used for studying activation of different Ras superfamily GTPases were: (a) pull down of activated Ras superfamily GTPases from cell lysates, by binding of the specific recombinant purified effector GTPase binding domains to the activated GTP bound form. Subsequent to the pull down of the activated GTPases, the proteins were detected and quantified by western blotting; (b) activation of GTPases effectors such as Raf or RAC, by reporter gene assays; and (c) direct immunoprecipitation kinase assays (FIG. 2).

Example 3

Detection of Apoptosis

The percentage of cells undergoing apoptosis was quantitatively determined using an Apoptosis Detection kit, on the basis of their ability to bind annexin V and exclude iodide, and also by an in situ cell detection kit incorporating HTC labeling and TUNEL.

Example 4

Cell Cycle Distribution

Cell cycle distribution studies were performed as previously described. Cells were trypsinyzed and suspended for 10 minutes at room temperature at 1.106/ml buffer containing 1mg/ml RNAse, 1% NP-40, 10 µg/ml propidium iodide and 0.1% sodium citrate. Propidium iodide fluorescence was measured using a FACStar plus flow cytometer equipped with an air-cooled argon laser delivering 15 mW of light at 488 nM. The red fluorescence from 1.104 cells from each sample was collected through a 610 nm bandpass filter.

Example 5

Identification of the Site of Molecular Interaction Between AS101 and p21ras Cysteine P21ras was cleaved by cyanogen bromide. This process yielded three fragments, each containing one cysteine residue: fragment 1 containing Cys51 (Mr 7,203); fragment 2 containing Cys60 (Mr 4,540) and fragment 3 containing Cys118 (Mr 6223). To confirm that Cys118 is the molecular target of AS101, a form of p21ras was generated identical to the wild type enzyme except that Cys118 is changed by a Ser residue (referred to as p21rasC118S). This modification only changed the sulfur atom of Cys118 to oxygen. The stimulation by AS101 of nucleotide exchange on GDP-preloaded p21rasC118S in vitro was determined.

Example 6

Evaluation of the Therapeutic use of AS101 Utilizing Rat Spinal Cord Injury Model Twenty rats were divided into 4 treatment groups (control, AS101 15; 20; 30 µg). Experimental spinal cord injury (SCI) was induced via weight-drop contusion models that result in significant locomotor deficits, including lack of coordination and trunk stability. AS101 was applied topically to the damaged area and rats were treated for 21 days with AS101 administrated i.v. At the end of the first week following SCI, and on days 14 and 21, recovery was determined using Basso, Beattie and Bresnahan (BBB) locomotor scale score.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating Parkinson's disease in a subject in need thereof, the method comprising administering to the subject a therapeutically effective amount of a tellurium-containing compound having general Formula I:

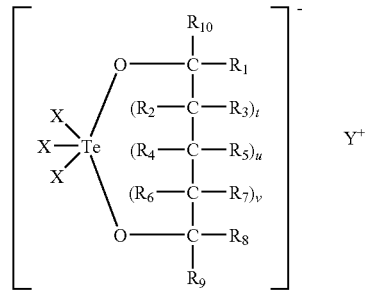

Formula I wherein:
t, u and v are each 0;
each of $R_1$, $R_8$, $R_9$ and $R_{10}$ is hydrogen;
X is chloro; and
Y is ammonium,
the compound being ammonium trichloro(dioxyethylene-O,O')tellurate (AS 101).

2. The method of claim 1, wherein said administering is effected by a route selected from the group consisting of oral, parenteral, rectal, topical, nasal or inhalation administration.

3. The method of claim 1, wherein said administering is effected orally.

4. The method of claim 1, wherein said administering is effected parenterally.

5. The method of claim 1, wherein said administering is effected by cerebro-vascular injection.

6. The method of claim 1, wherein said therapeutically effective amount ranges from about 0.1 mg/m²/day to about 20 mg/m²/ day.

7. The method of claim 1, wherein said at least one tellurium-containing compound forms a part of a pharmaceutical composition, said pharmaceutical composition further comprising a pharmaceutically acceptable carrier.

* * * * *